United States Patent
Medina Padilla et al.

(10) Patent No.: US 9,469,618 B2
(45) Date of Patent: Oct. 18, 2016

(54) THIADIAZOLIDINEDIONES AS GSK-3 INHIBITORS

(71) Applicant: ASD THERAPEUTICS PARTNERS LLC, Warren, NJ (US)

(72) Inventors: Miguel Medina Padilla, Tres-Cantos-Madrid (ES); Juan Manuel Domínguez Correa, Tres-Cantos-Madrid (ES); Javier de Cristobal Blanco, Tres-Cantos-Madrid (ES); Ana Fuertes Huerta, Tres-Cantos-Madrid (ES); Jorge Sánchez-Quesada, Tres-Cantos-Madrid (ES); Javier López Ogalla, Tres-Cantos-Madrid (ES); Susana Herrero Santos, Tres-Cantos-Madrid (ES); María Ángeles Pérez de la Cruz Moreno, Tres-Cantos-Madrid (ES); Olga Martínez Montero, Tres-Cantos-Madrid (ES); Beatriz Rodríguez Salguero, Tres-Cantos-Madrid (ES); Francisco Palomo Nicolau, Tres-Cantos-Madrid (ES)

(73) Assignee: ASD THERAPEUTICS PARTNERS, LLC, Warren, NJ (US)

( * ) Notice: Subject to any disclaimer, the term of this patent is extended or adjusted under 35 U.S.C. 154(b) by 0 days.

(21) Appl. No.: 15/155,437

(22) Filed: May 16, 2016

(65) Prior Publication Data

US 2016/0257660 A1 Sep. 8, 2016

Related U.S. Application Data

(62) Division of application No. 14/380,623, filed as application No. PCT/EP2013/053554 on Feb. 22, 2013, now Pat. No. 9,371,299.

(30) Foreign Application Priority Data

Feb. 24, 2012 (EP) .................................... 12382066

(51) Int. Cl.
C07D 285/08 (2006.01)
C07D 417/06 (2006.01)
(52) U.S. Cl.
CPC ........... *C07D 285/08* (2013.01); *C07D 417/06* (2013.01)
(58) Field of Classification Search
CPC ........................... C07D 285/08; C07D 417/06
See application file for complete search history.

(56) References Cited

U.S. PATENT DOCUMENTS 9,371,299 B2 6/2016 Padilla et al.
2008/0033012 A1 2/2008 Gil et al.
2009/0233971 A1 9/2009 Padilla et al.

FOREIGN PATENT DOCUMENTS

KR 837785 B1 6/2008
WO 0185685 A1 11/2001
WO 2005097117 A1 10/2005

OTHER PUBLICATIONS

CAS Registry No. 1350207-15-6, which entered STN on Dec. 7, 2011.*
Nasim, S. et al.; "N-Chlorosuccinimide is a convenient oxidant for the synthesis of 2, 4-disubstituted 1, 2, 4-thiadiazolidine-3, 5-diones," Tetrahedron Letters, 2009, pp. 257-259, vol. 50.
Martinez, A., et al.; "First Non-ATP Competitive Glycogen Synthase Kinase 3β(GSK-3β) Inhibitors: Thiadiazolidinones (TDZD) as Potential Drugs for the Treatment of Alzheimer's Disease," Journal of Medicinal Chemistry, 2002, pp. 1292-1299, vol. 45.
Turner, Emma A., et al.; "Small Molecule Inhibitors of Regulators of G Protein Signaling (RGS) Proteins," ACS Medicinal Chemistry Letters, 2012, pp. 146-150, vol. 3.
International Search Report, Mar. 20, 2013.
CAS Registry No. 1350207-15-6, STN on Dec. 7, 2011.
Machine translation of KR 837785 B1; http://eng.kipris.or.kr/enghome/main.jsp, Jan. 23, 2015.
Martinez, Ana, et al.; "SAR and 3D-QSAR Studies on Thiadiazolidinone Derivatives: Exploration of Structural Requirements for Glycogen Synthase Kinase 3 Inhibitors," J. Med. Chem., 2005, pp. 7103-7112, vol. 48.
Kang, Nam Sook, et al.; "Identification of small molecules that inhibit GSK-3 beta through virtual screening," Bioorganic & Medicinal Chemistry Letters, 2009, pp. 533-537, vol. 19.

* cited by examiner

*Primary Examiner* — Matthew Coughlin
(74) *Attorney, Agent, or Firm* — Tristan A. Fuierer; Moore & Van Allen, PLLC

(57) ABSTRACT

The present invention relates to new thiadiazolidinediones of formula (I), or any pharmaceutically acceptable salt, solvate or prodrug thereof, and its use in the treatment of a disease in which glycogen synthase kinase 3 (GSK-3) is involved, particularly neurodegenerative diseases, inflammatory and autoimmune diseases and cardiovascular disorders. Additionally, there is provided a process for preparing such compounds, as well as pharmaceutical compositions comprising them.

9 Claims, No Drawings

THIADIAZOLIDINEDIONES AS GSK-3 INHIBITORS

CROSS REFERENCE TO RELATED APPLICATIONS

This application is filed under the provisions of 35 U.S.C. §121 and is a divisional of U.S. patent application Ser. No. 14/380,623, filed on Aug. 22, 2014 and entitled "THIADIAZOLIDINEDIONES AS GSK-3 INHIBITORS" in the name of Miguel MEDINA PADILLA, et al., which claims priority to International Patent Application No. PCT/EP2013/053554, filed on Feb. 22, 2013, which claims priority to European Patent Application No. 12382066.4, filed on Feb. 24, 2012.

FIELD OF THE INVENTION

The present invention relates to new thiadiazolidinediones and its use in the treatment and/or prophylaxis of a disease in which glycogen synthase kinase 3 (GSK-3) is involved, particularly neurodegenerative diseases, inflammatory and autoimmune diseases and cardiovascular disorders. Additionally, there is provided a process for preparing such compounds, as well as pharmaceutical compositions comprising them.

BACKGROUND

Glycogen Synthase Kinase-3 (GSK-3)

Glycogen synthase kinase-3 (GSK-3) is a serine/threonine protein kinase comprised of α and β isoforms that are each encoded by distinct genes (*Chemistry & Biology*, 2000, 7(10), 793-803. *Selective small molecule inhibitors of glycogen synthase kinase-3 modulate glycogen metabolism and gene transcription*. Coghlan et al.; *Curr. Opinion Genetics Dev.*, 2000, 10(5), 508-514. *GSK3, a master switch regulating cell-fate specification and tumorigenesis*. Kim, L. & Kimmel, A. R.). GSK-3 plays critical roles in development, metabolic homeostasis, neuronal growth and differentiation, cell polarity, cell fate and in modulation of apoptotic potential.

Pathologies Related to Glycogen Synthase Kinase-3 (GSK-3)

Dysregulation (usually increase) of GSK-3 activity is believed to play a role in different and important disorders like neurodegenerative disorders [*Physiol. Rev.*, 2004, 84, 361-84. *Role of tau protein in both physiological and pathological conditions*. Ávila, J. et al.], cardiovascular disease [*Circ Res.*, 2009, 104(11), 1240-52; *Role of glycogen synthase kinase-3beta in cardioprotection*. Juhaszova M et al.; *Circ J.*, 2009, 73(7), 1184-92. *GSK-3beta, a therapeutic target for cardiomyocyte protection*. Miura T & Miki T], diabetes [*Trends. Mol. Med.*, 2002, 8, 126-32. *Glycogen synthase kinase 3: an emerging therapeutic target*. Eldar-Finkelman, H.] or viral infections [*Virus Res.*, 2008, 132, 160-73. *Residues in human respiratory syncytial virus P protein that are essential for its activity on RNA viral synthesis*. Asenjo, A. et al.].

Regarding neurodegenerative disorders and other CNS pathologies, GSK-3 dysregulation has been related to Alzheimer's disease [*Brain Res Bull.*, 2009, 80 (4-5), 248-50. *The role of GSK3 in Alzheimer disease*. Hernández F. et al.], mild cognitive impairment [*J Psychiatr Res.*, 2011, 45(2), 220-4. *Increased platelet GSK3B activity in patients with mild cognitive impairment and Alzheimer's disease*. Forlenza O. V. et al.], Parkinson's disease [*Neuroscience Letters* 2009, 449(2), 103-107. *Glycogen synthase kinase-3beta is associated with Parkinson's disease*. Masahiro N. & Hideaki H.], frontotemporal dementia [*Arch. Neurol.*, 2008, 65, 1368-74. *Association of GSK3B with Alzheimer disease and frontotemporal dementia*. Schaffer, B. et al.], frontotemporal lobar degeneration associated with Pick bodies [*Int J Alzheimers Dis.*, 2011, 2011, 352805. *Functional implications of glycogen synthase kinase-3-mediated tau phosphorylation*. Hanger D. P. & Noble W.], Pick's disease, progressive supranuclear palsy, subacute sclerosing panencephalitis, postencephalitic parkinsonism, dementia pugilistica, guam parkinsonism-dementia complex, corticobasal degeneration, argyrophilic grain disease, familial frontotemporal dementia and parkinsonism linked to chromosome 17 due to mutations in the tau gene (FTDP-17-tau) and other tauopathies [*Brain Research Reviews*, 2000, 33, 95-130. *Tau protein isoforms, phosphorylation and role in neurodegenerative disorders*. Buée, L. et al.], AIDS associated dementia [*J Neuroimmune Pharmacol.*, 2007, 2(1), 93-96. *Glycogen synthase kinase 3 beta (GSK-3 beta) as a therapeutic target in neuroAIDS*. Dewhurst S. et al.], Huntington's disease [*J Biol Chem.*, 2002, 277(37), 33791-8. *Glycogen synthase kinase-3beta inhibitors prevent cellular polyglutamine toxicity caused by the Huntington's disease mutation*. Carmichael J. et al.], Lewy body disease [*Neuropathology*, 2003, 23(3), 199-202. *Glycogen synthase kinase-3beta phosphorylates synphilin-1 in vitro*. Tanji K et al.], bipolar disorder [*Neurosci Biobehav Rev.*, 2007, 31(6), 920-931; *GSK-3 is a viable potential target for therapeutic intervention in bipolar disorder*. Roew M. K. et al.; *Bipolar Disord.*, 2002, 4(2), 137-144. *Glycogen Synthase Kinase-3β, mood stabilizers, and neuroprotection*. Li X et al.], depression [*J Pharmacol Sci.*, 2009, 110(1), 14-28. *Lithium and neuropsychiatric therapeutics: neuroplasticity via glycogen synthase kinase-3beta, beta-catenin, and neurotrophin cascades*. Wada A.], schizophrenia [*Drug News Perspect.*, 2007, 20(7), 437-45. *The role of glycogen synthase kinase-3beta in schizophrenia*. Koros E. & Dorner-Ciossek C.; *Trends Neurosci.*, 2007, 30(4), 142-9. *Schizophrenia as a GSK-3 dysregulation disorder*. Lovestone S. et al.], epilepsy [*J Neurochem.*, 1999, 72(3), 1327-30. *The mood-stabilizing agent valproate inhibits the activity of glycogen synthase kinase-3*. Chen G. et al.], mood disorders [*Curr Drug Targets.*, 2006, 7(11), 1421-34. *Glycogen synthase kinase-3 (GSK3) in psychiatric diseases and therapeutic interventions*. Jope R. S. & Roh M. S.], autism [*Proc Natl Acad Sci USA.*, 2008, 105(4), 1333-8. *Role of GSK3 beta in behavioral abnormalities induced by serotonin deficiency*. Beaulieu J. M. et al.], attention deficit hyperactivity disorder [*Proc Natl Acad Sci USA.*, 2004, 101(14), 5099-104. *Lithium antagonizes dopamine-dependent behaviors mediated by an AKT/glycogen synthase kinase 3 signaling cascade*. Beaulieu J. M. et al.], Down's syndrome [*FASEB J.*, 2008, 22(9), 3224-33. *Overexpression of Dyrk1A contributes to neurofibrillary degeneration in Down syndrome*. Liu F. et al.], fragile X syndrome (FXS) [*Biochem Pharmacol.*, 2010, 79(4), 632-46. *Lithium ameliorates altered glycogen synthase kinase-3 and behavior in a mouse model of fragile X syndrome*. Yuskaitis C. J. et al.], diseases associated with ischemia/reperfusion and shock [*Shock.*, 2007, 27(2), 113-23. *Glycogen synthase kinase 3beta as a target for the therapy of shock and inflammation*. Dugo L. et al.], brain injury [*Neurol Res.*, 2001, 23(6), 588-92. *Different expression of glycogen synthase kinase-3beta between young and old rat brains after transient middle cerebral artery occlusion. Sasaki C. et al.], multiple sclerosis [*Trends Immunol.*, 2010, 31(1), 24-31. *Innate and adaptive immune responses regulated by glycogen synthase kinase-3 (GSK3)*. Beurel E. et al.] and other autoimmune and inflammatory diseases afflicting the CNS [*J. Immunol.*, 2008, 181(1), 338-45. *Lithium prevents and ameliorates experimental autoimmune encephalomyelitis*. De Sarno P. et al.], spinocerebellar ataxia type 1 [*PLoS Med*, 2007, 4(5), 836-847. *Lithium therapy improves neurological function and hippocampal dendritic arborization in a spinocerebellar ataxia type 1 mouse model*. Watase K et al.], cerebral bleeding for example, due to solitary cerebral amyloid angiopathy [*Neuroscience.*, 2008, 153(2), 414-27. *Accumulation of beta-amyloid in the brain microvessels accompanies increased hyperphosphorylated tau proteins following microsphere embolism in aged rats*. Han F. et al.], amyotrophic lateral sclerosis [*Brain Res.*, 2008, 1196, 131-139. *Upregulation of GSK3β expression in frontal and temporal cortex in ALS with cognitive impairment (ALSci)*. Yang W. et al.], prion disease [*Biochem J.*, 2003, 15, 372 (Pt 1), 129-36. *Prion peptide induces neuronal cell death through a pathway involving glycogen synthase kinase 3*. Pérez M et al.], Gerstman-Sträussler-Scheinker disease [*BMC Infect Dis.*, 2010, 1, 10, 86. *Changes of tau profiles in brains of the hamsters infected with scrapie strains 263 K or 139 A possibly associated with the alteration of phosphate kinases*. Wang G. R. et al.], Hallervorden-Spatz disease and multiple systems atrophy [*Cell Mol Neurobiol.*, 2008, 28(1), 21-33. *Overexpressed alpha-synuclein regulated the nuclear factor-kappaB signal pathway*. Yuan Y. et al.] or myotonic dystrophy [*Cell Cycle.* 2009, 8, 15, 2356-9. *GSK3beta-cyclin D3-CUGBP1-eIF2 pathway in aging and in myotonic dystrophy*. Jin J. et al.].

In addition to its possible relevance to prevent neurodegeneration, GSK3 inhibitors may also be useful to foster other forms of neuronal repair, including axon regeneration [*J. Neurosci.*, 2008, 28, 8914-28. *Inactivation of glycogen synthase kinase 3 promotes axonal growth and recovery in the CNS*. Dill, J. et al.].

During the last few years, GSK-3 has been identified as a regulator of many components of the immune system, suggesting it might be a plausible therapeutic target in inflammatory and autoimmune diseases, such as chronic inflammatory diseases including rheumatoid arthritis, inflammatory bowel disease and psoriasis [*Eur J Biochem.*, 2001, 268(19), 5001-10. *The role of protein phosphorylation in human health and disease*. Cohen P.], arthritis [*Clin. Immunol.*, 2006, 120, 57-67. *Glycogen synthase kinase-3b inhibition attenuates the degree of arthritis caused by type II collagen in the mouse*. Cuzzocrea, S. et al.], peritonitis [*Immunity*, 2006, 24, 563-574. *IFN-g suppresses IL-10 production and synergizes with TLR2 by regulating GSK3 and CREB/AP-1 proteins*. Hu, X et al.], systemic inflammation, renal dysfunction and hepatotoxicity in endotoxemia [*Crit. Care Med.*, 2005, 33, 1903-1912. *GSK-3b inhibitors attenuate the organ injury/dysfunction caused by endotoxemia in the rat*. Dugo, L. et al.], asthma [*Am J Physiol Lung Cell Mol Physiol.*, 2009, 296(2), L176-84. *Airway smooth muscle hyperplasia and hypertrophy correlate with glycogen synthase kinase-3 (beta) phosphorylation in a mouse model of asthma*. Bentley J. K. et al.], sepsis [*J. Biochem. Cell. Biol.*, 2005, 37, 2226-2238. *GSK-3b inhibitors reduce protein degradation in muscles from septic rats and in dexamethasone treated myotubes. Int. Evenson, A. R. et al.]*, colitis [*Br. J. Pharmacol.*, 2006, 147, 575-582. *Reduction of experimental colitis in the rat by inhibitors of glycogen synthase kinase-3b*. Whittle, B. J. et al.], inflammation-induced organ injury caused by hemorrhage and resuscitation [*Shock*, 2006, 25, 485-491. *Glycogen synthase kinase-3b inhibitors protect against the organ injury and dysfunction caused by hemorrhage and resuscitation*. Dugo, L. et al.], inflammatory injury in chronic renal allograft disease [*Am J Transplant.*, 2008, 8(9), 1852-63. *Glycogen synthase kinase 3beta: a novel marker and modulator of inflammatory injury in chronic renal allograft disease*. Gong R. et al.] or lupus [*Int. J. Immunopharmacol.*, 1995, 17, 581-592. *Lithium chloride enhances survival of NZB/W lupus mice: influence of melatonin and timing of treatment*. Lenz, S. P. et al.].

Among cardiovascular disorders related to GSK-3 are heart disease [*Circ. Res.*, 2002, 90, 1055-63. *Glycogen synthase kinase-3beta: a novel regulator of cardiac hypertrophy and development*. Hardt, S. E. & Sadoshima, J.], atherosclerosis [*Am J Pathol.*, 2009, 174(1), 330-42. *Valproate attenuates accelerated atherosclerosis in hyperglycemic apoE-deficient mice: evidence in support of a role for endoplasmic reticulum stress and glycogen synthase kinase-3 in lesion development and hepatic steatosis*. Bowes A. J. et al.], hypertension [*J. Clin. Invest.*, 2002, 109(3), 373-381. *Fas receptor signaling inhibits glycogen synthase kinase 3β and induces cardiac hypertrophy following pressure overload*. Badorff C. et al.], restenosis [*Cardiovasc Res.*, 2010, Epub. *Delayed Re-endothelialization with Rapamycin-coated Stents is Rescued by the Addition of a Glycogen Synthase Kinase 3 Beta Inhibitor*. Ma X et al.] or leukopenia [Gallicchio, V. S. (1991) in *Lithium and the Cell*, ed. Birch, N J. (Academic, San Diego), pp. 185-198.].

Additional pathologies associated with GSK-3 are metabolic syndrome X [*Curr Pharm Des.*, 2004, 10(10), 1105-37. *Discovery and development of GSK3 inhibitors for the treatment of type 2 diabetes*. Wagman A. S. et al.], hair loss [*J Clin Invest.*, 2010, 120(2), 446-56. *Neural Wiskott-Aldrich syndrome protein modulates Wnt signaling and is required for hair follicle cycling in mice*. Lyubimova A. et al.], severe acute respiratory syndrome coronavirus [*J Biol Chem.*, 2009, 284(8), 5229-39. *Glycogen synthase kinase-3 regulates the phosphorylation of severe acute respiratory syndrome coronavirus nucleocapsid protein and viral replication*. Wu C. H. et al.], cocaine addiction [*J Neurochem.*, 2009, 111(6), 1357-68. *Glycogen synthase kinase 3beta in the nucleus accumbens core mediates cocaine-induced behavioral sensitization*. Xu C. M. et al.], bone loss [*Life Sci.*, 2009, 85 (19-20), 685-92. *Inhibition of glycogen synthase kinase-3beta attenuates glucocorticoid-induced bone loss*. Wang F. S. et al.] or glaucoma [*J Clin Invest.*, 2008, 118(3), 1056-64. *Increased expression of the WNT antagonist sFRP-1 in glaucoma elevates intraocular pressure*. Wang W. H. et al.].

GSK-3 Inhibitors

For a further review of GSK-3 inhibitors and their use as potential treatments for these pathologies, please reference to *Nature Reviews*, 2004, 3, 479-487. *GSK3 inhibitors: development end therapeutic potential*. Cohen, P. & Goedert, M; *Mini-Reviews in Medicinal Chemistry*, 2009, 9(9), 1024-1029. *GSK3 Inhibitors and Disease*. Hernández, F. et al.; *Curr. Opin. Drug Discov. Develop.*, 2008, 11(4), 533-543. *Glycogen synthase kinase-3 (GSK-3) inhibitors reach the clinic*. Medina, M & Castro, A.; John Wiley & Sons, Inc., 2006. *Glycogen Synthase Kinase 3 (GSK-3) and its inhibitors*. Chapter 14. Eds: Martinez, A., Castro, A. & Medina, M.

Several GSK-3 inhibitors like indirubines [*J. Biol. Chem.*, 2001, 276, 251-60. *Indirubins inhibit glycogen synthase* kinase-3 beta and CDK5/p25, two protein kinases involved in abnormal tau phosphorylation in Alzheimer's disease. A property common to most cyclin-dependent kinase inhibitors?*. Leclerc, S. et al.], maleimides [*Bioorg. Med. Chem. Lett.,* 2001, 11, 635-9. *3-Anilino-4-arylmaleimides: potent and selective inhibitors of glycogen synthase kinase-3 (GSK-3)*. Smith, D. et al.], 3-amino pyrazoles [*Bioorg. Med. Chem. Lett.,* 2003, 13, 1581-4. *5-arylpyrazolo[3, 4-b]pyridazines: potent inhibitors of glycogen synthase kinase-3 (GSK-3)*. Witherington, J. et al.], paullones [*Eur. J Biochem.,* 2000, 267, 5983-94. *Paullones are potent inhibitors of glycogen synthase kinase-3beta and cyclin-dependent kinase 5/p25.* Leost, M et al.], thiazoles [*J. Biol. Chem.,* 2003, 278, 45937-45. *Structural insights and biological effects of glycogen synthase kinase 3-specific inhibitor AR-A*014418. Bhat, R. et al.] or thiadiazolidinones [*J. Med. Chem.,* 2002, 45, 1292-9. *First non-ATP competitive glycogen synthase kinase 3 beta (GSK-3beta) inhibitors: thiadiazolidinones (TDZD) as potential drugs for the treatment of Alzheimer's disease.* Martinez, A. et al.].

There is still a need to find better GSK-3 inhibitors, being both effective and selective, and having improved physicochemical and pharmaceutical properties related to absorption, distribution, metabolism and excretion.

Thiadiazolidinediones

Small heterocyclic thiadiazolidinediones, irreversible GSK-3 inhibitors, have been proposed as new disease-modifying agents for the effective treatment of Alzheimer's disease and other pathologies and this relevant fact confers a remarkable interest to these compounds.

Some thiadiazolidinediones were firstly disclosed as GSK-3 inhibitors in the International Patent Application WO 01/85685. Subsequently, additional thiadiazolidinediones have been disclosed for example in J. 5 Med. Chem. 2002, 45, 1292-1299 and WO 05/97117.

BRIEF DESCRIPTION OF THE INVENTION

A new family of thiadiazolidinediones has been found which, in addition to show the ability to inhibit GSK-3, they also exhibit a remarkably better solubility, bioavailability and pharmacokinetic properties, thus making these compounds significantly better candidates for its use as drugs in the treatment of pathologies related to glycogen synthase kinase-3.

Accordingly, in a first aspect the present invention relates to a compound of Formula (I):

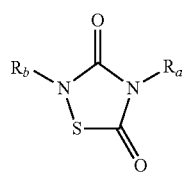

wherein:
$R_a$ is an alkyl group having from 1 to 3 carbon atoms, optionally substituted with hydroxyl, heterocyclyl or C(O)OR', wherein R' is an alkyl group;
$R_b$ is —(CHR$_1$)$_n$—(Z)$_m$-aryl;
$R_1$ is selected from hydrogen, alkyl or C(O)OR", wherein R" is an alkyl group;

Z is —C(R$_2$)(R$_3$)—, wherein R$_2$ and R$_3$ are independently selected from hydrogen and alkyl;
n is 0 or 1;
m is 1 or 2;
or any pharmaceutically acceptable salt, solvate or prodrug thereof.

A second aspect of the present invention refers to a process for the preparation of a compound of Formula (I) which comprises:
1) the reaction of a isothiocyanate of formula (II):

with sulfuryl chloride or chlorine,
to form the corresponding N—Ra-S-chloroisothiocarbamoyl chloride intermediate;
wherein Ra is as defined above,
and
2) the addition of an isocyanate of formula (III):

wherein Rb is as defined above.

Another aspect of the invention relates to a pharmaceutical composition comprising a compound of Formula (I), or a salt, solvate or prodrug thereof, as defined above.

An additional aspect of the present invention refers to a compound of Formula (I), or a salt, solvate or prodrug thereof, for its use as a medicament.

Another aspect of the invention relates to a compound of Formula (I), or a salt, solvate or prodrug thereof, for its use in the treatment of a cognitive, neurodegenerative or neurological disease or condition.

A further aspect of the present invention refers to a compound of Formula (I), or a salt, solvate or prodrug thereof, for its use in the treatment of a disease or condition selected from diabetes, inflammatory and autoimmune diseases, cardiovascular disorders, and pathologies selected from metabolic syndrome X, hair loss, severe acute respiratory syndrome coronavirus, cocaine addiction, bone loss and glaucoma.

An additional aspect of the present invention is the use of a compound of Formula (I) as defined above, or a salt, solvate or prodrug thereof, in the preparation of a medicament for the treatment of a cognitive, neurodegenerative or neurological disease or condition.

A further aspect of the present invention is the use of a compound of Formula (I) as defined above, or a salt, solvate or prodrug thereof, in the preparation of a medicament for the treatment of a disease or condition selected from diabetes, inflammatory and autoimmune diseases, cardiovascular disorders, and pathologies selected from metabolic syndrome X, hair loss, severe acute respiratory syndrome coronavirus, cocaine addiction, bone loss and glaucoma.

Another aspect of the present invention is a method of treating a cognitive, neurodegenerative or neurological disease or condition, comprising administering to a patient in need of such treatment a therapeutically effective amount of a compound of Formula (I) as defined above, or a salt, solvate or prodrug thereof.

An additional aspect of the present invention is a method of treating a disease selected from diabetes, inflammatory and autoimmune diseases, cardiovascular disorders, and pathologies selected from metabolic syndrome X, hair loss, severe acute respiratory syndrome coronavirus, cocaine addiction, bone loss and glaucoma, comprising administering to a patient in need of such treatment a therapeutically effective amount of a compound of Formula (I) as defined above, or a salt, solvate or prodrug thereof.

Finally, another aspect of the invention relates to the use of a compound of formula (I) as defined above, or a salt, solvate or prodrug thereof, as a reactive in an in vitro biological assay requiring inhibition of GSK-3.

DETAILED DESCRIPTION OF THE INVENTION

Definitions

"Alkyl" refers to a linear or branched hydrocarbon chain radical, said chain consisting of 1 to 6 carbon atoms, preferably, 1 to 3 carbon atoms, containing no insaturation, and which is attached to the rest of the molecule by a single bond, e. g., methyl, ethyl, n-propyl, i-propyl, n-butyl, t-butyl, n-pentyl, etc.

"Aryl" refers to an aromatic ring system. According to one embodiment, aryl groups comprise 6 to 14 carbon atoms, more particularly 6 to 10, even more particularly 6 carbon atoms. According to an embodiment, aryl is a phenyl, naphthyl, indenyl, fenanthryl or anthracyl radical, preferably phenyl or naphthyl radical.

"Heterocyclyl" refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

In a particular embodiment of the invention, the aryl radical in the substituent $R_b$ is phenyl.

In another particular embodiment, m is 1. In this particular embodiment, $R_2$ and $R_3$ are preferably hydrogen.

In another particular embodiment n is 0.

In another particular embodiment n is 1. In this particular embodiment, $R_1$ is preferably —CO(O)R", wherein R" is an alkyl group, more preferably is ethyl.

In another particular embodiment, $R_a$ is ethyl or methyl. More preferably, $R_a$ is ethyl.

In another particular embodiment, Ra is ethyl or methyl, optionally substituted with hydroxyl, heterocyclyl or —C(O)OR', wherein R' is an alkyl group.

More preferably, $R_a$ is ethyl optionally substituted with hydroxyl or is methyl optionally substituted with a heterocyclyl or —C(O)OR'. Even more preferably, R' is ethyl. The heterocyclyl is preferably a 4- to 8-membered ring with one heteroatom selected from nitrogen, oxygen or sulfur, more preferably is tetrahydrofurane.

In a preferred embodiment of the invention, the aryl radical in the substituent $R_b$ is phenyl, m is 1, $R_2$ and $R_3$ are hydrogen, n is 1 and $R_1$ is —CO(O)R", wherein R" is an alkyl group, more preferably is ethyl. In this preferred embodiment, $R_a$ is methyl optionally substituted with —C(O)OR', wherein R' is an alkyl group, more preferably is ethyl.

In another preferred embodiment of the invention, the aryl radical in the substituent $R_b$ is phenyl, m is 1, $R_2$ and $R_3$ are hydrogen, and n is 0. In this preferred embodiment, $R_a$ is ethyl or methyl optionally substituted with hydroxyl or heterocyclyl. The heterocyclyl is preferably a 4- to 8-membered ring with one heteroatom selected from nitrogen, oxygen or sulfur, more preferably is tetrahydrofurane.

Preferred compounds of the invention are selected from the following compounds:

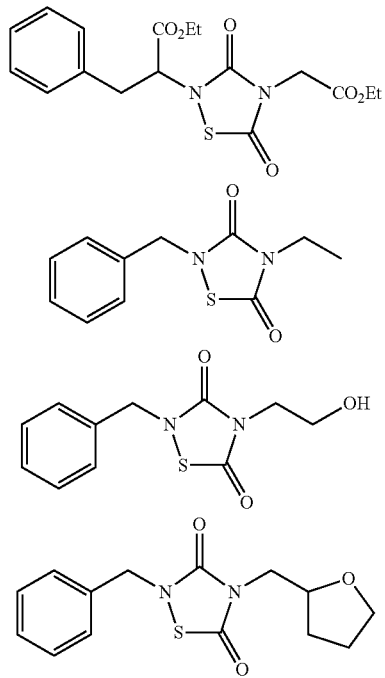

Synthesis of the Compounds of the Invention

The compounds of the invention can be synthesized by available procedures [Martinez, A. Et al., *Bioorg. Med. Chem.*, 1997, 5, 1275-1283].

In a particular embodiment, the compounds of formula (I) were prepared following the procedure depicted in scheme 1, and using the reactivity of N-alkyl-S-chloroisothiocarbamoyl chlorides with different alkyl isocyanates.

Squeme 1

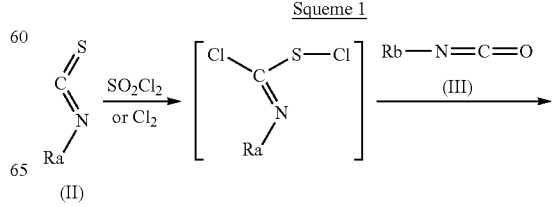

-continued

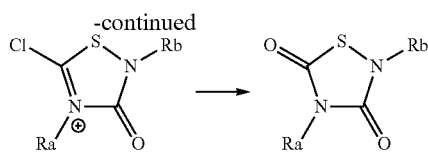

Thus, the process of the invention comprises:
1) the reaction of a isothiocyanate of formula (II):

with sulfuryl chloride or chlorine,
to form the corresponding N—Ra-S-chloroisothiocarbamoyl chloride intermediate;
wherein Ra is as defined above,
and
2) the addition of an isocyanate of formula (III):

wherein Rb is as defined above.

In a particular embodiment, the step 1) (isothiocyanate chlorination) is performed by addition of an equimolecular quantity of sulfuryl chloride or chlorine into a solution of the corresponding isothiocyanate of formula (II) in anhydrous dichloromethane or n-heptane. Preferably, this reaction takes place at −10° C. under inert atmosphere. The step 2) is also performed under the same conditions of temperature and atmosphere.

Subsequently, the reaction mixture is allowed to reach room temperature and finally is hidrolized.

In another particular embodiment, the step 1 is performed in the absence of any solvent, i.e. by direct addition of an equimolecular quantity of sulfuryl chloride or chlorine over the corresponding isothiocyanate of formula (II). This reaction also takes place preferably at −10° C. under inert atmosphere. Optionally, the $SO_2$ formed is removed from the mixture and the residue is dissolved in n-heptane. After the addition of the corresponding isocyanate of formula (III), the solid formed is separated and stirred in a mixture of n-heptane and water.

Medical Uses

According to a preferred embodiment, the cognitive, neurodegenerative or neurological disease or condition in the above uses and methods of treatment is selected from Alzheimer's disease, Parkinson's disease, mild cognitive impairment, frontotemporal dementia, frontotemporal lobar degeneration associated with Pick bodies, Pick disease, progressive supranuclear palsy, subacute sclerosing panencephalitis, postencephalitic parkinsonism, dementia pugilistica, guam parkinsonism-dementia complex, corticobasal degeneration, argyrophilic grain disease, familial frontotemporal dementia and parkinsonism linked to chromosome 17 due to mutations in the tau gene (FTDP-17-tau), AIDS associated dementia, Huntington's disease, Lewy body disease, bipolar disorder, depression, schizophrenia, epilepsy, mood disorders, autism, attention deficit hyperactivity disorder, Down's syndrome, fragile X syndrome (FXS), ischemia/reperfusion, shock, brain injury, multiple sclerosis, autoimmune and inflammatory diseases afflicting the CNS, spinocerebellar ataxia type 1, cerebral bleeding due to solitary cerebral amyloid angiopathy, amyotrophic lateral sclerosis, prion disease, Gerstman-Sträussler-Scheinker disease, Hallervorden-Spatz disease, multiple systems atrophy and myotonic dystrophy.

According to a preferred embodiment, the inflammatory and autoimmune disease or condition in the above uses and methods of treatment is selected from rheumatoid arthritis, inflammatory bowel disease, psoriasis, arthritis, peritonitis, systemic inflammation, renal dysfunction, hepatotoxicity in endotoxemia, asthma, sepsis, colitis, inflammation-induced organ injury caused by hemorrhage and resuscitation, inflammatory injury in chronic renal allograft disease and lupus.

According to a preferred embodiment, the cardiovascular disorders in the above uses and methods of treatment are selected from heart disease, atherosclerosis, hypertension, restenosis and leukopenia.

The term "pharmaceutically acceptable salts" refers to salts which, upon administration to the recipient are capable of providing (directly or indirectly) a compound as described herein. The preparation of salts can be carried out by methods known in the art. Preferably, "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, non aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

The term "prodrug" as used in this application is defined here as meaning a chemical compound having undergone a chemical derivation such as substitution or addition of a further chemical group to change (for pharmaceutical use) any of its physico-chemical properties, such as solubility or bioavailability, e.g. ester and ether derivatives of an active compound that yield the active compound per se after administration to a subject. Examples of well known methods of producing a prodrug of a given acting compound are known to those skilled in the art and can be found e.g. in Krogsgaard-Larsen et al., Textbook of Drug design and Discovery, Taylor & Francis (April 2002).

Particularly favoured prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

The term "solvate" according to this invention is to be understood as meaning any form of the active compound according to the invention which has another molecule (most likely a polar solvent) attached to it via a non-covalent bonding. Examples of such solvates include hydrates and alcoholates, e.g. methanolates.

The preparation of salts, solvates and prodrugs can be carried out by methods known in the art. It will be appreciated that non-pharmaceutically acceptable salts, solvates or prodrugs also fall within the scope of the invention since those may be useful in the preparation of pharmaceutically acceptable salts, solvates or prodrugs.

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of the present invention may exhibit tautomerism. Tautomers are one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include compounds which differ only in the presence of one or more isotopically enriched atoms. For example, compounds having the present structures except for the replacement of an hydrogen by a deuterium or tritium, or the replacement of a carbon by a $^{13}$C- or $^{14}$C-enriched carbon or $^{15}$N-enriched nitrogen are within the scope of this invention.

Generally a "therapeutically effective amount" of the compound of the invention or a pharmaceutical composition thereof will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The term "treatment" or "to treat" in the context of this specification means administration of a compound or formulation according to the invention to prevent, ameliorate or eliminate the disease or one or more symptoms associated with said disease. "Treatment" also encompasses preventing, ameliorating or eliminating the physiological sequelae of the disease.

The term "ameliorate" in the context of this invention is understood as meaning any improvement on the situation of the patient treated—either subjectively (feeling of or on the patient) or objectively (measured parameters).

Pharmaceutical Compositions

The present invention further provides pharmaceutical compositions comprising a compound of Formula (I) of the present invention, or a salt, solvate or prodrug thereof, and at least one pharmaceutically acceptable carrier, adjuvant, and/or vehicle, for administration to a patient.

The term "excipient" refers to components of a drug compound other than the active ingredient (definition obtained from the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions (U.S. National Library of Medicine. National Institutes of Health). Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker, © 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin.

According to a preferred embodiment, the pharmaceutical composition may further contain a therapeutically effective amount of one or more compounds useful for the treatment and/or prophylaxis of cognitive, neurodegenerative or neurological diseases or conditions. According to another embodiment, the pharmaceutical composition may further contain a therapeutically effective amount of one or more compounds selected from the group comprising beta secretase inhibitors or modulators including BACE1 protein inhibitors, amyloid beta-protein inhibitors, including immunoglobulins, antiamyloid monoclonal antibodies and vaccines, amyloid beta-protein precursor inhibitors, gamma secretase inhibitors or modulators, muscarinic receptor modulators, acetylcholinesterase inhibitors, butyrilcholinesterase inhibitors, Choline acetyltransferase stimulants, HMG-CoA reductase inhibitors, non-steroidal antiinflammatory agents, cyclo-oxygenase 2 inhibitors, N-methyl-D-aspartate receptor antagonists, vitamin E, nicotinic acetylcholine receptor modulators, serotonin receptor modulators, cannabinoid receptor agonists, CB1 receptor inverse agonists or CB1 receptor antagonists, AMPA receptor modulators, GABA receptor modulators, inhibitors of amyloid aggregation, glycogen synthase kinase beta inhibitors, promoters of alpha secretase activity, phosphodiesterase 9A and 10 inhibitors, type 4 cyclic nucleotide phosphodiesterase inhibitors, estrogen and cholesterol absorption inhibitors, 11-beta hydroxysteroid dehydrogenase type 1 inhibitors, adenosine receptor antagonists, adrenergic receptor modulators, advanced glycosylation end-product receptor antagonists, alpha-synuclein inhibitors, antioxidants, free radical scavengers, apolipoprotein A stimulants, apolipoprotein E agonists, apoptosis inhibitors, calcium channel modulators, sodium channel modulators, calpain inhibitors, cathepsin B inhibitors, cell-replacements including stem-cell-therapies, glial cell line-derived neurotrophic factor agonists, nerve growth factor stimulants, chelating agents, complement factor D inhibitors, cyclic AMP response element-binding protein stimulants, D amino acid oxidase inhibitors, dopamine receptor agonists and dopamine uptake inhibitors, endopeptidase inhibitors, fibroblast growth factor stimulants, G protein-coupled receptor antagonists, gene expression stimulants, glucose stimulants, metabotropic glutamate receptor modulators, histamine H3 receptor antagonists or inverse agonists, histone deacetylase inhibitors, mitochondrial-permeability-transition pore-modulators, monoamine oxidase B inhibitors, neuropeptide stimulants, neurotransmitter modulators, plasminogen activator inhibitor-1 inhibitors, protein kinase C stimulants, rho-associated kinase inhibitors, ribonucleotide reductase inhibitors, signal transduction pathway inhibitors, superoxide dismutase stimulants, tau protein modulators, tubulin polymerisation promoters, toll-like receptor agonists, transglutaminase inhibitors and Wnt protein modulators.

Examples of pharmaceutical compositions include any solid (tablets, pills, capsules, granules etc.) or liquid (solutions, suspensions or emulsions) composition for oral, topical or parenteral administration, among others.

Pharmaceutical dosage forms include but are not limited to parenteral preparations (such as injections, powders for injections, implants, etc), liquid preparations for oral use (such us syrups, solutions, suspensions, emulsions, powders and granules for suspension and for solution, oral drops, etc), oromucosal preparations (such as lozenges, sublingual and buccal tablets, oromucosal drops and sprays, etc) solid preparations for oral use (oral powders, effervescent powders, tablets—uncoated, coated, effervescent, soluble, dispersible, orodispersible, modified release, gastro-resistant-, oral lyophilisates, capsules—hard, soft, modified release, gastro-resistant-, granules—coated, effervescent, modified release, gastro-resistant-), transdermal patches, powders for inhalation, nasal preparations and rectal preparations.

In a preferred embodiment the pharmaceutical compositions are in oral form because of the convenience for the patient and the chronic character of many of the diseases to be treated. Said oral pharmaceutical compositions may contain conventional excipients known in the art, such as:

Film Coated Tablet:
  Binders, such as maize starch, pregelatinised maize starch, povidone, gelatine, etc
  Diluents or fillers, such as microcrystalline cellulose, lactose, sodium phosphate, calcium phosphate dibasic dihydrate, calcium phosphate dibasic anhydrous (Emcompress, Di-tab, Di-cal-fos), etc
  Disintegrants, such as sodium croscarmellose (Acdisol, Explocel, Vivasol), sodium starch glycolate (Glycolis, Explotab, Primojel, Vivastar), cross-linked povidone, gums, etc.
  Glidants, such as talc or colloidal silica.
  Lubricants, such as magnesium stearate, stearic acid, sodium stearyl fumarate, etc
  Film-formers, such as hydroxypropylcellulose (Klucel, Metocel), Hypromellose (Metocel, Metolose, Pharmacoat), hydroxy-propylmethylcellulose, etc
  Opacifiers, such as titanium dioxide.
  Colouring agents, such as sunset yellow, iron oxides, indigo carmine, erythrosine, etc
  Plasticizers, such as polyethyleneglycol, triacetin, etc Powder for Oral Solution (POS) in Sachet
  Acidifying agents, such as citric acid.
  Buffering agents, such as citric acid, sodium citrate
  Diluents or fillers, such as mannitol (Pearlitol), sorbitol (Neosorb, Parteck), sucrose, maltose (Advantose), etc
  Sweetening agents, such as sucralose, aspartame, accesulfame, sodium saccharine, etc
  Glidants, such as colloidal silicon dioxide (Aerosil, Cabosil, Aeroperl)
  Flavouring agents, such as strawberry flavour, lemon flavour, cola flavour, orange flavour, etc
  Thickening or stabilisers such as modified celluloses (hydroxipropylcellulose, carboxymethylcellulose sodium, . . . ), povidones, gums, etc Syrup
  Antimicrobial and solvent agents, such as ethanol, propyleneglycol, etc.
  Sweetening agents, such as sorbitol or sucrose
  Antimicrobial preservative, such as sodium benzoate, potassium sorbate
  Acidifying agents, such as citric acid or ascorbic acid
  Buffering agents, such as citric acid and sodium citrate, phosphates, acetic acid and sodium acetate.
  Flavouring agents, such as vanilla flavour, strawberry flavour, cola flavour, peach flavour, etc
  Colouring agents, such as tartrazine, curcumin, quinoline yellow, sunset yellow, etc Capsules
  Diluents, such as microcrystalline cellulose, lactose, calcium carbonate, calcium phosphate dibasic, calcium phosphate monobasic, calcium sulphate
  Disintegrants, such as sodium starch glycolate, cross-linked povidone.
  Lubricants, such as talc, magnesium stearate, stearic acid, sodium stearyl fumarate, polyethylenglycols, etc.

Gastrorresistant Capsules
  Capsule fillers, such as microcrystalline cellulose, sugar spheres.
  Binders and film formers, such as copolymers methacrylate acid, polymeric methacrylates (Eudragit, Kollicoat)
  Plasticizers and film formers such as dibutylphthalate
  Colouring agents, such as erythrosine, sunset yellow, indigo carmine, etc
  Solvents, such as acetone, isopropyl alcohol, etc The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating. Particular examples are given below.

The pharmaceutical compositions may also be adapted for parenteral administration, such as sterile solutions, suspensions or lyophilized products in the appropriate unit dosage form. Adequate excipients can be used, such as:
  Antimicrobial preservatives, such as methylparaben, propylparaben, etc.
  Antioxidants, such as sodium metabisulfite, propyl gallate, etc
  Stabilizing and suspending agents, such as soluble or swellable modified celluloses, e.g. carboxymethylcellulose sodium (Aquasorb, Blanose, Nymcel)
  Tonicity agents, such as sodium chloride
  Solubilizers, such as propyleneglycol or polyethyleneglycols Particular examples are given below.

The mentioned formulations will be prepared using standard methods such as those described or referred to in the Spanish and US Pharmacopoeias and similar reference texts.

In the following, the present invention is further illustrated by examples. They should in no case be interpreted as a limitation of the scope of the invention as defined in the claims.

EXAMPLES

Preparation of the Compounds

Example 1

General Procedures

Method A:

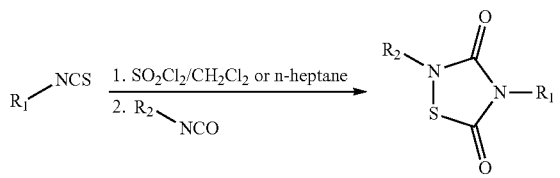

Sulfuryl chloride (1 eq) was added into a solution of the corresponding isothiocyanate (1 eq) in anhydrous dichloromethane or n-heptane (30 volumes), at −10° C. under inert atmosphere and vigorous stirring. The reaction could be followed by NMR monitoring the formation of the N-alkyl-S-chloroisothiocarbamoyl chloride intermediate until completion. After 2 h of stirring at −10° C., the corresponding isocyanate (1 eq) was added into the initial mixture, under the same conditions. The final reaction mixture was stirred for 18 h, allowing it to reach room temperature gradually. Finally the mixture was hydrolyzed by the addition of water (15 volumes) and the two layers were separated. The organic layer was washed with water and brine, separated and dried with anhydrous $Na_2SO_4$, filtered and evaporated to dryness. The residue was purified by flash chromatography or by precipitation.

Method B:

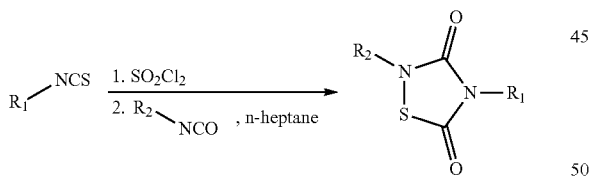

Sulfuryl chloride (1 eq) was slowly added (5 minutes) over the corresponding isothiocyanate (1 eq) under inert atmosphere at −10° C. The reaction could be followed by NMR monitoring the formation of the N-alkyl-S-chloroisothiocarbamoyl chloride intermediate until completion (2 hours at −10° C.). Then, $SO_2$ was removed from the mixture under vacuum at 30° C. and the residue was dissolved in n-heptane (10 volumes) and cooled to −10° C. The corresponding isocyanate was added (1 eq) and the mixture was stirred for 18 h, allowing it to reach room temperature gradually. The solid formed was filtered and vigorously stirred in a mixture of n-heptane (10 volumes) and water (20 volumes), filtered again and washed with n-heptane (10 volumes) and dried to yield the pure product.

Method C:

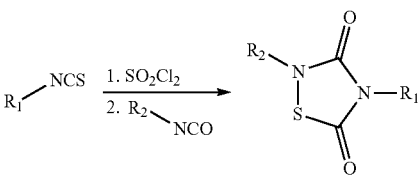

Sulfuryl chloride (1 eq) was slowly added (5 minutes) over the corresponding isothiocyanate (1 eq) under inert atmosphere at −10° C. The reaction could be followed by NMR monitoring the formation of the N-alkyl-S-chloroisothiocarbamoyl chloride intermediate until completion. After 2 h of stirring at −10° C. the corresponding isocyanate (1 eq) was added at −10° C. and the mixture was stirred for 18 h, allowing it to reach room temperature gradually. The solid formed was filtered and vigorously stirred in a mixture of n-heptane (10 volumes) and water (20 volumes), filtered again and washed with n-heptane (10 volumes) and dried to yield the pure product.

Following the above general procedure, the following compounds according to the invention were prepared:

TABLE 1

| Compound No. | Structure |
| --- | --- |
| Compound 1 | 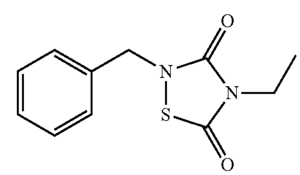 [SMILES: CCn1c(=O)sn(Cc2ccccc2)c1=O] |
| Compound 2 | 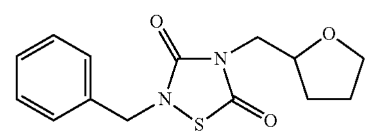 [SMILES: O=c1sn(Cc2ccccc2)c(=O)n1CC1CCCO1] |
| Compound 3 | 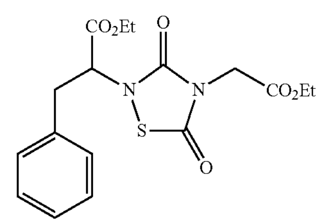 [SMILES: CCOC(=O)Cn1c(=O)sn(C(Cc2ccccc2)C(=O)OCC)c1=O] |
| Compound 4 | 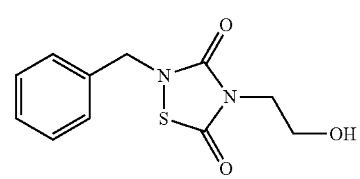 [SMILES: O=c1sn(Cc2ccccc2)c(=O)n1CCO] |

In the following, the particular reagents necessary for obtaining the above compounds, the characterization of some derivatives formed during the reactions, as well as their experimental spectral data, are indicated.

Example 2

Preparation of 2-benzyl-4-ethyl-[1,2,4]thiadiazolidine-3,5-dione (Compound 1)

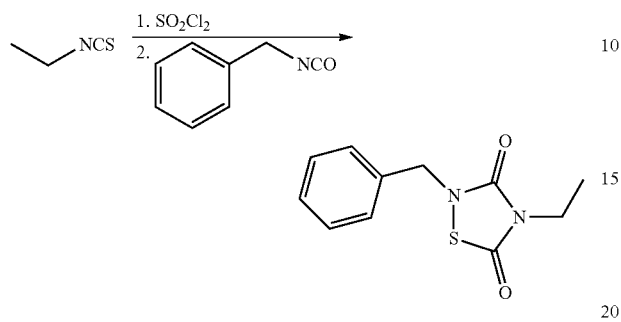

Method A:

Reaction performed in methylene chloride. Intermediate formation was followed by NMR. The final product was isolated by precipitation in n-heptane. White solid. 70% yield.

$^1$H NMR (400 MHz, CDCl$_3$, δ ppm): 7.37 (m, 3H), 7.31 (m, 2H), 4.78 (s, 2H), 3.77 (q, J=7.18 Hz, 2H), 1.29 (t, J=7.17 Hz, 3H).

$^{13}$C NMR (100 MHz, CDCl$_3$, δ ppm): 165.83, 153.07, 134.56, 129.01, 128.77, 128.43, 48.60, 37.84, 13.17.

MS (ES$^+$): m/z=237 (M+H)$^+$

Example 3

Preparation of 2-benzyl-4-(tetrahydro-furan-2-ylm-ethyl)-[1,2,4]thiadiazolidine-3,5-dione (Compound 2)

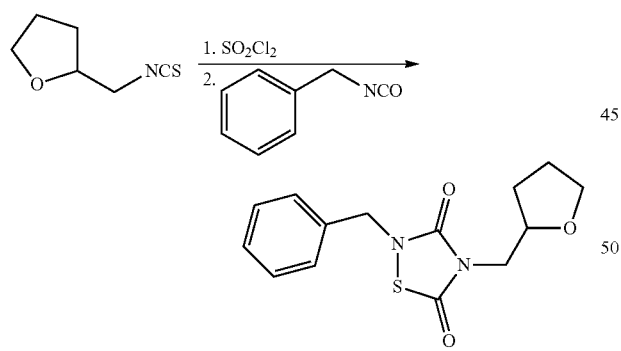

Method A:

Reaction performed in n-heptane. Intermediate formation was followed by NMR. The final product was isolated as a colorless oil that was filtered through SiO$_2$ and eluted with a mixture of ethyl acetate and n-heptane (1:2). The resulting oil slowly precipitates at 0° C. to yield the final product as a white solid. 74% yield.

Method A:

Reaction performed in methylene chloride. Intermediate formation was followed by NMR. The final product was isolated as a colorless oil that was filtered through SiO$_2$ and eluted with a mixture of ethyl acetate and n-heptane (1:2). The resulting oil slowly precipitates at 0° C. to yield the final product as a white solid. 73% yield.

$^1$H NMR (400 MHz, DMSO-d$_6$, δ ppm): 7.36 (m, 5H), 4.80 (AB System, S$_{AB}$=15.6 Hz, 2H), 4.12 (m, 1H), 3.67 (m, 3H), 3.54 (dd, J=13.79, 4.90 Hz, 1H), 1.85 (m, 3H), 1.60 (m, 1H).

$^{13}$C NMR (100 MHz, DMSO-d$_6$, δ ppm): 165.65, 152.77, 135.42, 128.69, 128.12, 127.96, 74.43, 66.88, 47.34, 45.50, 28.42, 24.68.

MS (ES$^+$): m/z=293 (M+H)$^+$

The N-alkyl-S-chloroisothiocarbamoyl chloride derivative formed from the reaction of the isothiocyanate and sulfuryl chloride was isolated and characterized by NMR:

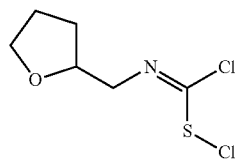 [SMILES: ClS/C(Cl)=N\CC1CCCO1]

$^1$H-NMR (400 MHz, CDCl$_3$, δ ppm): 4.16 (m, 1H), 3.85 (m, 1H), 3.71 (m, 1H), 3.65 (d, J=4.9 Hz, 2H), 1.85 (m, 3H), 1.65 (m, 1H).

Preparation of 2-benzyl-4-(2-hydroxy-ethyl)-[1,2,4]thiadiazolidine-3,5-dione (Compound 3)

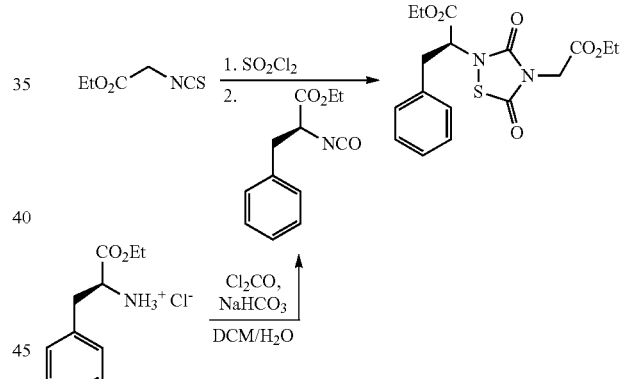

Example 4

Synthesis of 2-isocyanato-3-phenyl-propionic acid ethyl ester (Intermediate)

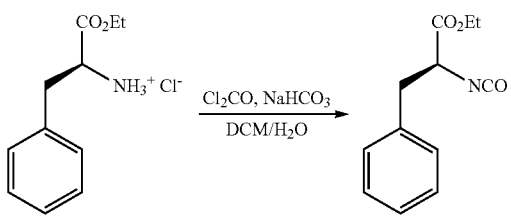

To an ice-cold suspension of L-phenylalanine ethyl ester hydrochloride (25.0 g, 109 mmol) in methylene chloride (800 mL) a saturated solution of sodium bicarbonate (800 mL) was added and the mixture was vigorously stirred at 0° C. for 30 minutes. Stirring was stopped to allow the separation of the two layers and a solution of phosgene in toluene (20%, 100 mL, 190 mmol) was added directly into the organic layer. Stirring was resumed while keeping the mixture at 0° C. for one hour and at room temperature for one additional hour. The organic layer was separated, and washed sequentially with water and a saturated solution of sodium chloride, dried with sodium sulphate, filtered and evaporated to yield a colorless oil that slowly solidifies (22.7 g, 95% yield).

$^1$H NMR (400 MHz, DMSO-d$_6$, δ ppm): 7.31 (m, 3H), 7.22 (m, 2H), 4.62 (dd, J=7.0, 5.0 Hz, 1H), 4.20 (q, J=7.07 Hz, 2H), 3.05 (ABX system, J$_{AB}$=13.8 Hz, 2H), 1.23 (t, J=7.12 Hz, 3H).

$^{13}$C NMR (100 MHz, DMSO-d$_6$, δ ppm): 170.30, 135.72, 129.26, 128.25, 126.94, 126.32, 62.06, 57.75, 38.45, 13.84.

Example 5

Synthesis of 2-benzyl-4-(2-hydroxy-ethyl)-[1,2,4]thiadiazolidine-3,5-dione (Compound 3)

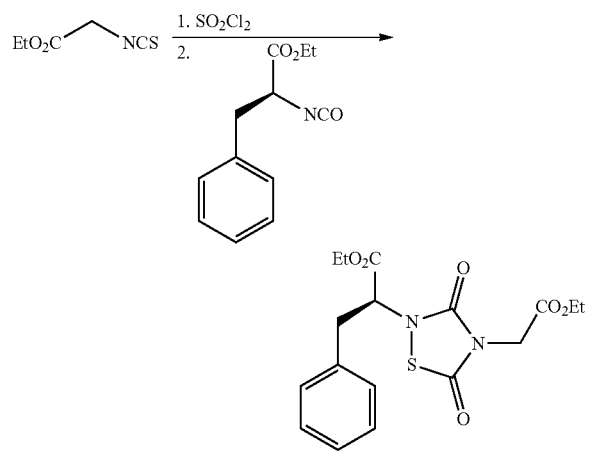

Method A:
Reaction performed in n-heptane. Intermediate formation was monitored by NMR and completed in 20 hours. The final product was isolated by precipitation in the reaction mixture, treated with a mixture of n-heptane and water, filtered and washed with n-heptane. White solid. 72% yield.

Method A:
Reaction performed in methylene chloride. Intermediate formation was monitored by NMR and completed in 2 hours. The final product was isolated as described above. White solid. 72% yield.

Method C:
Intermediate formation was monitored by NMR and completed in 3 hours. The final product was isolated as described above. White solid. 84% yield.

$^1$H NMR (400 MHz, DMSO-d$_6$, δ ppm): 7.27 (m, 5H), 5.26 (dd, J=10.3, 5.3 Hz, 1H), 4.34 (AB System, S$_{AB}$=17.2 Hz, 2H), 4.14 (m, 4H), 3.32 (dd, J=14.5, 5.3 Hz, 1H), 3.10 (dd, J=14.5, 10.3 Hz, 1H), 1.18 (t, J=7.1 Hz, 3H), 1.18 (t, J=7.1 Hz, 3H).

$^{13}$C NMR (100 MHz, DMSO-d$_6$, δ ppm): 168.53, 166.38, 165.59, 152.13, 135.60, 128.89, 128.39, 126.93, 61.63, 61.40, 57.68, 42.34, 35.38, 13.81, 13.77.

MS (ES$^+$): m/z=381 (M+H)$^+$

The N-alkyl-S-chloroisothiocarbamoyl chloride derivative formed from the reaction of the isothiocyanate and sulfuryl chloride was characterized by NMR:

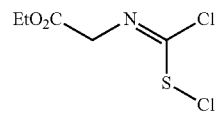 [SMILES: CCOC(=O)C/N=C(/Cl)SCl]

$^1$H-NMR (400 MHz, CDCl$_3$, δ ppm): 4.43 (s, 2H), 4.24 (q, J=7.2 Hz, 2H), 1.30 (t, J=7.1 Hz, 3H).

$^{13}$C-NMR (100 MHz, CDCl$_3$, δ ppm): 163.63, 139.28, 61.57, 54.52, 14.11

Preparation of 2-benzyl-4-(2-hydroxy-ethyl)-[1,2,4]thiadiazolidine-3,5-dione (Compound 4)

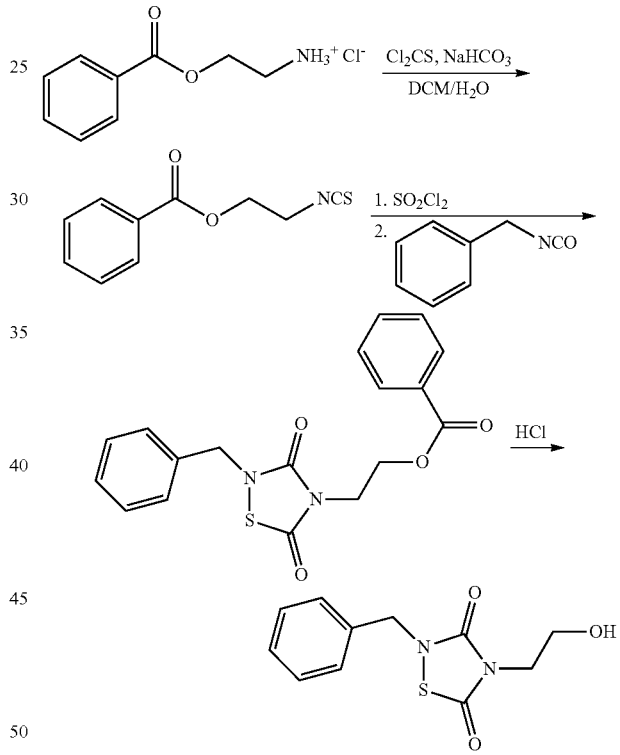

Example 6

Synthesis of benzoic acid 2-isothiocyanato-ethyl ester (Intermediate)

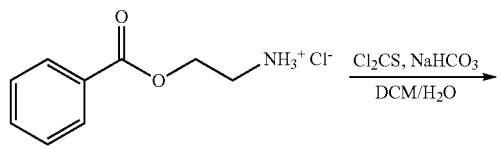

-continued

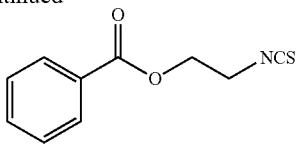
5

To an ice-cold suspension of benzoic acid 2-amino-ethyl ester hydrochloride (50.0 g, 248 mmol) in methylene chloride (600 mL) a saturated solution of sodium bicarbonate (600 mL) was added and the mixture was vigorously stirred at 0° C. for 15 minutes. Stirring was stopped to allow the separation of the two layers and thiophosgene (38.0 mL, 498 mmol) was added directly into the organic layer. Stirring was resumed and the mixture was allowed to reach room temperature. After 3 hours the organic layer was separated, and washed sequentially with water and a saturated solution of sodium chloride, dried with sodium sulphate, filtered and evaporated to yield the desired pure isothiocyanate as pale yellow oil (49.5 g, 96% yield).

$^1$H NMR (400 MHz, DMSO-d$_6$, δ ppm): 8.01 (m, 2H), 7.69 (tt, J=7.4, 1.2 Hz, 1H), 7.56 (t, J=7.4 Hz, 2H), 4.50 (t, J=4.8 Hz, 2H), 4.06 (t, J=4.8 Hz, 2H).

$^{13}$C NMR (100 MHz, DMSO-d$_6$, δ ppm): 165.22, 133.53, 129.14, 129.10, 128.72, 62.62, 44.42.

Example 7

Synthesis of benzoic acid 2-(2-benzyl-3,5-dioxo-[1,2,4]thiadiazolidin-4-yl)-ethyl ester (Intermediate)

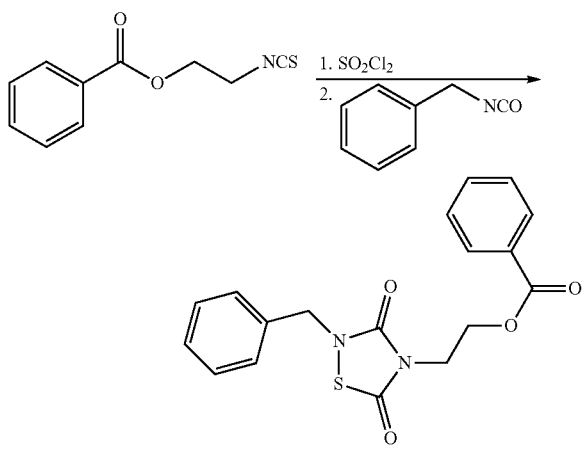

Method A:
Reaction performed in methylene chloride. The final product was isolated by flash chromatography on SiO$_2$ (hexane 0% to 30% of ethyl acetate). 73% yield.

Method B:
The final product was obtained as a white solid. 85% yield.

Method C:
The final product was isolated as a white solid. 92% yield.

$^1$H NMR (400 MHz, DMSO-d$_6$, δ ppm): 7.93 (m, 2H), 7.66 (tt, J=7.6, 1.2 Hz, 1H), 7.51 (m, 2H), 7.32 (m, 3H), 7.26 (m, 2H), 4.79 (s, 2H), 4.50 (t, J=5.2 Hz, 2H), 4.02 (t, J=5.2 Hz, 2H).

$^{13}$C NMR (100 MHz, DMSO-d$_6$, δ ppm): 165.75, 165.48, 152.55, 135.40, 133.32, 129.25, 129.11, 128.59, 128.03, 127.78, 61.25, 47.20, 41.20.

The N-alkyl-S-chloroisothiocarbamoyl chloride derivative formed from the reaction of the isothiocyanate and sulfuryl chloride employing Method B was isolated and characterized by NMR:

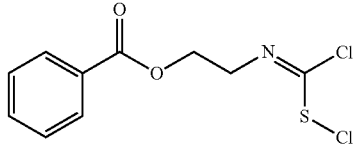 [SMILES: O=C(OCC/N=C(/Cl)SCl)c1ccccc1]

$^1$H-NMR (400 MHz, CDCl$_3$, δ ppm): 8.04 (dd, J=1.5, 8.2 Hz, 2H), 7.57 (m, 1H), 7.44 (m, 2H), 4.59 (t, J=5.6 Hz, 2H), 4.03 (t, J=5.6 Hz, 2H).

$^{13}$C-NMR (100 MHz, CDCl$_3$, δ ppm): 166.61, 136.27, 133.34, 130.12, 129.91, 128.63, 63.36, 52.67.

Example 8

Synthesis of 2-benzyl-4-(2-hydroxy-ethyl)-[1,2,4]thiadiazolidine-3,5-dione (Compound 4)

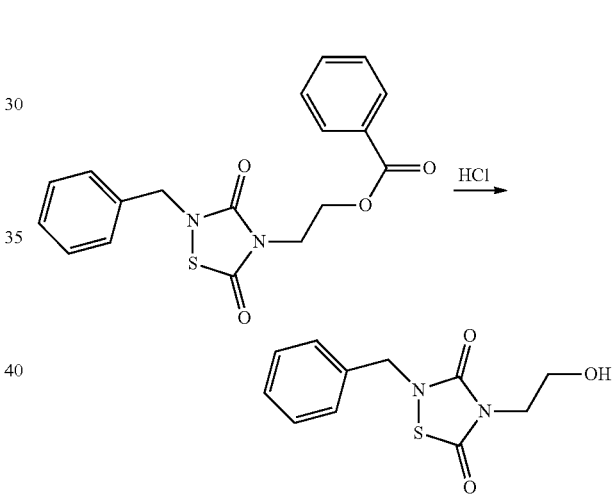

To a suspension of benzoic acid 2-(2-benzyl-3,5-dioxo-[1,2,4]thiadiazolidin-4-yl) ethyl ester (74.0 g, 207.6 mmol) in methanol (740 mL) 12N HCl (740 mL) was added at room temperature. The mixture was heated at 50° C. for 18 h, then additional 12N HCl (250 mL) was added and the mixture was stirred for 84 hours at 40° C. until hydrolysis was completed. The mixture was concentrated at reduced pressure to remove the methanol, and the resulting mixture was extracted with methylene chloride (3×500 mL). The combined organic layers were dried (Na$_2$SO$_4$), filtered and evaporated to yield an oil that was treated with hot ethyl acetate (200 mL) and precipitated by the addition of n-heptane (200 mL) to yield the pure desired product as a white solid (42.5 g, 81%)

$^1$H NMR (400 MHz, DMSO-d$_6$, δ ppm): 7.41-7.31 (m, 5H), 4.91 (t, J=5.85 Hz, 1H), 4.80 (s, 2H), 3.66 (m, 2H), 3.58 (m, 2H).

$^{13}$C NMR (100 MHz, DMSO-d$_6$, δ ppm): 165.77, 152.87, 135.47, 128.67, 128.09, 127.96, 57.08, 47.33, 44.58.

MS (ES$^+$): m/z=253 (M+H)$^+$

Biological Data

Example 9

GSK-3 Assay

The enzymatic activity of GSK3β was determined with a commercial system based on the Z'-LYTE® technology, available from Life Technologies (Carlsbad, Calif., USA), using human recombinant GSK3β (N-terminal 6His-tagged recombinant enzyme with an H350L mutation) from Millipore (Billerica, Mass., USA) as the enzyme source. This technology utilizes the fluorescence resonance energy transfer ("FRET") process between fluorescein and coumarin. The assay principle is based on the differential sensitivity of phosphorylated and non-phosphorylated peptide to proteolytic cleavage, which precludes the energy transfer process between the two fluorophores attached to both sides of the cleavage site. Hence, phosphorylation by GSK3β will yield a phosphopeptide, which cannot be hydrolyzed by a suitable protease and energy transfer between the two fluorophores will occur. Opposingly, lack of phosphorylation will cause peptide hydrolysis hence lack of energy transfer. The assay is performed in 384-well black plates, in a final volume of 10 µl, with 2 nM enzyme concentration in 50 mM Hepes pH 7.5, 50 mM $MgCl_2$, 5 mM EGTA and 0.05% Brij-35, using 12.5 µM ATP and 2 µM substrate peptide. The latter is a synthetic peptide, provided by Invitrogen under the commercial name "Ser/Thr 9 peptide", and it is based upon the sequence of a GSK3β substrate protein (glycogen synthase I) containing Ser-641. The peptide is labeled at both ends with fluorescein and coumarin. The assay is carried out in the presence of different concentrations of the tested compound, at a final 1% (v/v) DMSO concentration. After a 60 min incubation at room temperature, 5 µl of a commercial protease solution (sold by the same vendor in the assay kit) is added and a subsequent 1 h incubation at room temperature is performed, before adding 5 µl of a suitable "stop solution", also provided by the vendor in the kit. After that, fluorescence intensity is recorded, monitoring emission at both 445 and 520 nm, upon excitation at 400 nm. An emission ratio is finally calculated, using the quotient among the emission at 445 nm divided by that at 520 nm.

In the assay plate, several wells are included as a control for full enzyme activity, these wells do not contain any inhibitor or tested substance. Likewise, several wells are also included as a control for lack of enzyme activity, thus these wells do not contain inhibitor nor enzyme. The emission ratio of each tested sample is normalized to that of the control wells, so that for every compound concentration the percentage of inhibition is calculated by using the following equation:

$$\% \text{ Inhibition} = 100 \cdot \frac{E - S}{E - B}$$

where "S" is the emission from the wells with the tested sample, "E" is the average emission from control wells with full enzyme activity and "B" is the average emission from wells with full enzyme inhibition. Inhibition values obtained for every compound concentration are finally used to calculate the pEC50 of the tested compound, this parameter being the negative value of the logarithm of the compound concentration, in M units, causing 50% of its maximum effect (i.e., the higher the pEC50 value the higher the potency of the compound). For that purpose the data were fitted to the following equation using the nonlinear regression function of GraphPad™ Prism 5.0 (GraphPad Software Inc.):

$$\% \text{ Inhibition} = L + \frac{H - L}{1 + 10^{(\log C + pEC50)N}}$$

where "L" is the lower asymptote of the theoretical sigmoidal curve, "H" is the higher asymptote, "C" is the concentration of compound in M units and "N" is the Hill coefficient.

In Table 2, the pEC50 values obtained for some compounds of Formula (I) are indicated:

TABLE 2

| Compound No. | Structure | GSK-3 inhibition pEC50 average |
|---|---|---|
| Compound 1 | See table 1 | 6.2 |
| Compound 2 | See table 1 | 5.7 |
| Compound 3 | See table 1 | 7.6 |
| Compound 4 | See table 1 | 5.8 |

Physicochemical Properties

Example 10

Thermodynamic Solubility of TDZDs

Thermodynamic solubility was determined in duplicate from samples with a compound concentration of 2 mg/mL in aqueous 0.01 M phosphate buffered saline (PBS) pH 7.4 with a mixing period of 24 hours. Analysis and quantification was performed by LC-UV. Calibration lines were prepared for each compound from samples at of 1.0, 0.1, 0.01 and 0.001 mg/mL concentration in acetonitrile.

In Table 3, the results obtained for some compounds of Formula (I) are indicated:

TABLE 3

| Compound No | Structure | Thermodynamic solubility (mg/mL) |
|---|---|---|
| Compound 1 | See table 1 | 0.617 |
| Compound 2 | See table 1 | 1.030 |
| Compound 3 | See table 1 | 0.022 |
| Compound 4 | See table 1 | 1.841 |
| Compound 5 (Comparative) | 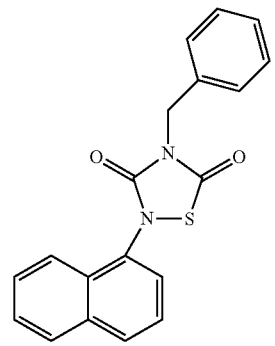 [SMILES: O=c1sn(-c2cccc3ccccc23)c(=O)n1Cc1ccccc1] | ≤0.001 |

These results clearly indicate that the compounds of the present invention show an improved thermodynamic solubility when compared with previous TDZD compounds (such as compound 5).

Pharmacokinetic Evaluations

Example 11

Brain and Plasma Exposition and Bioavailability

Pharmacokinetic behaviour in mice was evaluated for some compounds of Formula (I) as well as with a previous TDZD as comparative compound (compound 5).

Male C57BL6J mice (20-25 g, 8 weeks old, Harlan) were used to perform the pharmacokinetics studies. Each drug was suspended in a mixture of 25% PEG 400, 15% cremophor and q.s. distilled water by oral gavage (dose 200 mg/kg). Blood and brain samples (n=2 mice per sample point) were collected at specified time points 0.25, 0.5, 1, 2, 4, 6, 8 and 24 hours after dosing. Intravenous administrations (dose 1 mg/kg) were also performed to determine bioavailability of the oral administration (time points 0.03, 0.08, 0.16, 0.5, 1, 2 and 4 hours; dose 1 mg/kg, 1 mL/kg)

Plasma sample analysis was performed by LC/MS/MS using $ESI^+$ after protein precipitation with ACN (0.1% formic acid). Brain samples were homogenised, extracted by liquid-liquid extraction with ACN/ethyl acetate (50:50), evaporate until dryness and reconstitute in 85/15 ACN/$H_2O$ (0.1% formic acid). After extraction, 20 µl were injected onto the LC/MS/MS system using a sunfire 3.5 µm, 2.1×100 mm column at 40° C. The mobile phase used for the elution contained ACN (0.1% formic acid) and water (0.1% formic acid) using appropriate gradient of 7 to 15 minutes at 0.5 mL/min. The following transitions were monitored for each of the compounds: Compound 1, 237.13>90.89 (3.5 kV, 12V); Compound 2, 293.12>90.97 (3 kV, 25V); Compound 3, 381.7>307.2 (3 KV, 15V); and Compound 4, 253.32>90.99 (3.5 kV, 10V). Pharmacokinetic modelling and parameter calculations were carried out using the WinNonlin® pharmacokinetic software package (version 5.2, Pharsight Corporation, Moutain View, Calif.) using a non-compartimental model.

The results obtained for the compounds of formula (I) as compared to comparative compound 5 showed a considerably improvement on the brain and plasma exposition and bioavailability. Plasmatic exposure (AUC; Area Under Curve) after oral administration were up to 4.5 higher than compound 5 and values of maximal concentration ($C_{max}$) nearly double in the most favourable cases. Brain exposure increased extensibility up to 18% (brain/plasma). Bioavailability was also higher for this family of compounds in parallel to its better solubility. The increased plasma and brain exposure could derive in reduction of dose to reach efficacy, thus making these compounds better candidates for its use as drugs in the treatment of pathologies related to GSK-3.

Pharmaceutical Compositions

In the following examples, the detailed preparation of some pharmaceutical compositions is described.

Example 12

Powder for Injectable Suspension

Composition:

| INJECTABLE | mg/ml | % |
|---|---|---|
| Active ingredient (Compound of Formula I) | 10 | 1 |
| Methylparaben | 1 | 0.1 |
| Prophylparaben | 0.1 | 0.01 |
| Propyleneglycol | 100 | 10 |
| Sodium metabisulfite | 0.25 | 0.025 |
| Sodium chloride | 8.5 | 0.85 |
| Water for injection | csp | |

Manufacturing Process:
Powder for Suspension
  Fill the active ingredient into vials
Diluent
  Dissolve methylparaben, prophylparaben, sodium metabilsulfite, sodium chloride in propyleneglycol. Mix for a suitable time
  Add water for injection and mix for a suitable time.
  Sterilise by filtration and fill into vials
  For final reconstitution before administration, put the diluent solution into the active ingredient vial and shake up to homogeneization.
  A list of suitable excipients for injectable suspensions has been detailed above.

Example 13

Film Coated Tablet

Composition:

| FILM COATED TABLETS | mg/tablet | % (over FCT) |
|---|---|---|
| Tablet Core: | | |
| Active ingredient (Compound of Formula I) | 400 | 55.5 |
| Microcrystalline cellulose | 136 | 18.9 |
| Povidone K-25 | 5 | 0.7 |
| Maize starch | 10 | 1.4 |
| Maize Starch, pregelatinised | 25 | 3.5 |
| Lactose | 100 | 13.9 |
| Sodium croscarmellose | 7 | 1.0 |
| Talc | 12 | 1.7 |
| Magnesium stearate | 5 | 0.7 |
| Total (core) | 700 | |
| Film coating: | | |
| Hypromellose | 8 | 1.1 |
| Titanium dioxide | 5 | 0.7 |
| Macrogol/PEG 4000 | 3 | 0.4 |
| Lactose | 4 | 0.6 |
| Total (tablet) | 720 | |

Manufacturing Process:
  Prepare granulation solution dissolving Povidone K-25 in water
  Mix the active ingredient, maize starch, maize starch pregelatinised and microcrystalline cellulose.
  Granulate with granulation solution
  Drying
  Sieve the dried granules through a suitable mesh size Add lactose, sodium croscarmellose and talc
Mix for a suitable time
Add magnesium stearate
Mix for a suitable time
Once final blend is finished, then is ready for tabletting.
Tablet compression
Film coating
A list of suitable excipients for coated tablets has been detailed above.

Example 14

Powder for Oral Solution (POS) in Sachet

Composition:

| POS-SACHETS | mg/sachet | % |
|---|---|---|
| Active ingredient (Compound of Formula I) | 500 | 9.9% |
| Citric acid | 150 | 3.0% |
| Sodium citrate | 100 | 2.0% |
| Manitol | 2500 | 49.5% |
| Sorbitol | 1500 | 29.7% |
| Sucralose | 150 | 3.0% |
| Aerosil 200 | 5 | 0.1% |
| Lemon flavour | 75 | 1.5% |
| Cola flavour | 75 | 1.5% |
| Total | 5,055 | |

Manufacturing Process:
 Pass all the components through a suitable mesh size
 Mix the components into a suitable mixer
 Discharge final blend into containers
 Dosage the blend into sachets
A list of suitable excipients for powders for oral solution has been detailed above.

Example 15

Syrup

Composition:

| SYRUP | mg/ml | % |
|---|---|---|
| Active ingredient (Compound of Formula I) | 5 | 0.5 |
| Propyleneglycol | 50 | 5 |
| Ethanol | 10 | 1 |
| Sorbitol | 250 | 25 |
| Sodium benzoate | 1.5 | 0.15 |
| Citric acid | 20 | 2 |
| Sodium citrate | 15 | 1.5 |
| Vainille flavour | 1.2 | 0.12 |
| Tartrazine | 30 | 3 |
| Purified water | csp | |
| Total | 380 | |

Manufacturing Process:
 Put propyleneglycol and ethanol in a suitable container
 Add sodium benzoate up to total dissolution
 Add citric acid and sodium citrate and mix up to total dissolution
 Add active ingredient and mix up to homogeneization
 Add sorbitol and mix up to homogeneization
 Add purified water and mix up to homogeneization
 Add vainille flavour and tartrazine and mix up to homogeneization
 Once the syrup bulk is finished, it is ready for dosing into glass or plastic bottles.
A list of suitable excipients for syrups has been detailed above.

Example 16

Capsules

Composition:

| CAPSULES | mg/capsule | % |
|---|---|---|
| Active ingredient (Compound of Formula I) | 400 | 66.7 |
| Microcrystalline cellulose | 85 | 14.2 |
| Calcium phosphate | 100 | 16.7 |
| Talc | 10 | 1.7 |
| Magnesium stearate | 5 | 0.8 |
| Total | 600 | |

Manufacturing Process:
 Pass all the components through a suitable mesh size
 Put active ingredient, cellulose microcrystalline, calcium phosphate and talc into a suitable mixer.
 Mix for a suitable time
 Add magnesium stearate
 Mix for a suitable time
 Once the final blend is finished, it is ready to be dosed into gelatin capsules (suitable size)
A list of suitable excipients for capsules has been detailed above.

Example 17

Gastrorresistant Capsules

Composition:

| GASTRORRESISTANT CAPSULES (pellets) | mg/capsule | % |
|---|---|---|
| Active ingredient (Compound of Formula I) | 40 | 10 |
| Microcrystalline cellulose spheres | 260 | 65 |
| Poloxamer | 15 | 3.8 |
| Copolymer methacrylic acid | 80 | 20.0 |
| Pftalate dibutyl | 2 | 0.5 |
| Erythrosine | 3 | 0.8 |
| Isopropyl alcohol | eliminated during process | |
| Acetone | eliminated during process | |
| Total | 400 | |

Manufacturing Process:
 Dissolve erythrosine, phthalate dibutyl and copolymer methacrylic acid in acetone+isopropylalcohol.
 Add active ingredient and the poloxamer and dissolve it in the previous solution.
 Put the microcrystalline cellulose spheres into a fluid bed dryer.
 Spray the coating solution over on the cellulose spheres.
 Once the coating solution has been totally sprayed, dry the granules.

The invention claimed is:

1. A compound of Formula (I):

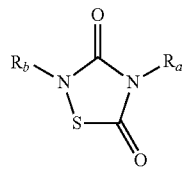

(I)

wherein:
R_a is an unsubstituted ethyl, or a methyl group or an ethyl group substituted with hydroxyl or heterocyclyl;
R_b—(Z)_m-aryl;
Z is —C(R_2)(R_3)—, wherein $R_2$ and $R_3$ are independently selected from hydrogen and alkyl;
m is 1 or 2;
or any pharmaceutically acceptable salt, solvate or prodrug thereof.

2. The compound according to claim 1, wherein the aryl radical in the substituent $R_b$ is phenyl.

3. The compound according to claim 1, wherein m is 1.

4. The compound according to claim 1, wherein $R_2$ and $R_3$ are hydrogen.

5. The compound according to claim 1, selected from the following compounds:

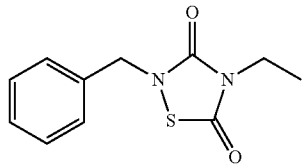

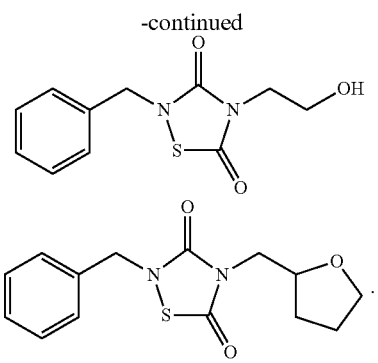

6. A pharmaceutical composition comprising a compound of Formula (I) as defined in claim 1, or a pharmaceutically acceptable salt, solvate or prodrug thereof, and at least one pharmaceutically acceptable carrier, adjuvant, and/or vehicle.

7. A composition comprising a compound of formula (I) as defined in claim 1, or a pharmaceutically acceptable salt, solvate or prodrug thereof, as a reactive in an in vitro biological assay requiring inhibition of GSK-3.

8. A method for the therapeutic treatment of a cognitive, neurodegenerative or neurological disease or condition, said method comprises the administration to a patient in need of such treatment of a therapeutic effective amount of a compound of Formula (I) as defined in claim 1, or a pharmaceutically acceptable salt, solvate or prodrug thereof.

9. A method for the therapeutic treatment of a disease or condition selected from diabetes, inflammatory and autoimmune diseases, cardiovascular disorders, and pathologies selected from metabolic syndrome X, hair loss, severe acute respiratory syndrome coronavirus, cocaine addiction, bone loss and glaucoma, said method comprises the administration to a patient in need of such treatment of a therapeutic effective amount of a compound of Formula (I) as defined in claim 1, or a pharmaceutically acceptable salt, solvate or prodrug thereof.

* * * * *